United States Patent
Shi et al.

(10) Patent No.: US 11,840,518 B2
(45) Date of Patent: *Dec. 12, 2023

(54) USE OF BROMOPHENOL-PYRAZOLINE COMPOUNDS FOR THE TREATMENT OF FELINE CORONAVIRUS DISEASES

(71) Applicant: Shandong Linghai Biotechnology Co., Ltd., Weihai (CN)

(72) Inventors: Dayong Shi, Weihai (CN); Xiangqian Li, Weihai (CN); Xin Wang, Weihai (CN); Feng Xu, Weihai (CN)

(73) Assignee: Shandong Linghai Biotechnology Co., Ltd., Weihai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/869,819

(22) Filed: Jul. 21, 2022

(65) Prior Publication Data

US 2022/0363644 A1    Nov. 17, 2022

(30) Foreign Application Priority Data

Oct. 13, 2021 (CN) .......................... 202111190625.5

(51) Int. Cl.
*C07D 231/06* (2006.01)
*A61P 31/14* (2006.01)

(52) U.S. Cl.
CPC ............ *C07D 231/06* (2013.01); *A61P 31/14* (2018.01)

(58) Field of Classification Search
CPC ............................. C07D 231/06; A61P 31/14
See application file for complete search history.

(56) References Cited

U.S. PATENT DOCUMENTS

| | | |
|---|---|---|
| 2009/0143454 A1 | 6/2009 | Maurer et al. |
| 2010/0280016 A1 | 11/2010 | Meyers et al. |
| 2012/0035131 A1 | 2/2012 | Meyers et al. |

*Primary Examiner* — Kamal A Saeed

(57) ABSTRACT

The present invention belongs to the field of medical technology, and specifically relates to use of bromophenol-pyrazoline compounds for the treatment of feline coronavirus diseases. Studies carried out for the present invention revealed that bromophenol-pyrazoline compounds could inhibit activity of feline infectious peritonitis virus main protease (FIPV $M^{pro}$) and interfere with replication of feline infectious peritonitis virus (FIPV) in cells. In a clinical trial, the bromophenol-pyrazoline compounds can treat infectious peritonitis in cats naturally infected with the FIPV, greatly improve survival rate of cats, and can be used to prepare drugs for treating feline infectious peritonitis.

9 Claims, 2 Drawing Sheets

USE OF BROMOPHENOL-PYRAZOLINE COMPOUNDS FOR THE TREATMENT OF FELINE CORONAVIRUS DISEASES

FIELD

The present invention belongs to the field of medical technology, and relates to a new use of bromophenol-pyrazoline compounds, in particular use of bromophenol-pyrazoline compounds for the prevention/treatment of feline coronavirus diseases.

BACKGROUND

Feline coronavirus (FCV), belonging to nido-viridae of coronaviridae, is an enveloped, non-segmented, single-stranded positive-strand RNA virus. Feline enteric coronavirus (FECV) is the most common FCV, is ubiquitous in cats worldwide, can be transmitted through fecal-oral route, but is not a serious pathogen itself. Approximately 5% of cats persistently infected with the FECV develop a highly lethal mutant feline infectious peritonitis virus (FIPV). The FIPV resulting from mutation of the FECV lose the ability to infect healthy cats, but has greatly increased pathogenicity and lethality.

The FIPV can replicate efficiently and sustainably in mononuclear phagocytes, and expand throughout the body as the mononuclear phagocytes circulate in the body, causing the host cat's immune system hyperreponsiveness, thus resulting in attack of diseases and death. Common sites of lesions of feline infectious peritonitis (FIP) are serosa, kidney, mesenteric lymph nodes, brain, eye, liver, spleen and lung, and clinical symptoms thereof comprise ascites, dyspnea, uveitis, ataxia, refractory fever, lethargy, anorexia, jaundice and weight loss.

The FIP is considered an "incurable disease" in the cat world, and failure to treat the FIP in a timely manner causes cats to typically die in two months or so, resulting in nearly 100% mortality. There is an FCoV vaccine in the United States and some European countries, and the vaccine can be administered intranasally against temperature-sensitive mutant strains of FCoV, but efficacy thereof is controversial. Since antibody-dependent enhancement was observed in an experiment, more vaccinated cats developed the FIP than the control group.

At present, there is no simple and definitive treatment for the FIP. Currently, supportive therapy with symptomatic drugs is mainly used to help cats overcome the disease by inhibiting virus replication, inhibiting inflammatory response, stimulating the immune system and reducing risk of reinfection. A nucleoside analog under development (GS-441524) was found to be useful in treating naturally infected FIP by directly interfering with virally encoded replication process. After 4 weeks of continuous treatment with GS-441524 at 4 mg/kg, about 60% of cats with the FIP were in remission. GS-441524 can be used to treat the FIP, but is characterized by high price (RMB 13,200 yuan per month), low cure rate and high relapse rate. Therefore, it is of great significance to develop an oral and highly effective new drug targeting the FIP.

Bromophenol-pyrazoline compounds were developed and designed by the inventors in previous studies to inhibit activity of novel human coronavirus, and have broad application prospects in preparation of drugs for the treatment of human coronavirus pneumonia. Subsequent studies revealed that such compounds have therapeutic effects on porcine epidemic diarrhea virus (PEDV) and porcine transmissible gastroenteritis virus (TGEV). Therefore, the bromophenol-pyrazoline compounds are a class of compounds with great pharmaceutical potential, and further discovery of novel pharmaceutical efficacy, especially the prevention/treatment of feline coronavirus diseases of the present invention, would be of great significance.

SUMMARY

In view of the above prior art, an object of the present invention is to provide new pharmaceutical use of bromophenol-pyrazoline compounds.

Studies carried out for the present invention revealed that the bromophenol-pyrazoline compounds can inhibit replication of feline infectious peritonitis virus (FIPV), can treat feline infectious peritonitis in clinical trials, can greatly improve survival rate of cats, and can be used to prepare drugs for treating feline coronavirus diseases.

In order to achieve the above object, the present invention uses the following technical solution:

The present invention provides use of a class of bromophenol-pyrazoline compounds in preparation of a drug for the treatment of feline coronavirus diseases.

In the above use, the bromophenol-pyrazoline compounds have a general structural formula shown in Formula I below:

wherein $R_1$, $R_2$, $R_3$, $R_4$ and $R_5$ are respectively selected from any of H, F, Br, OH and $OCH_3$;

$R_6$ is selected from any of H, CHO, $COCH_3$, $COCH_2CH_3$, $COCH_2CH_2CH_3$, $COOCH_3$, $COOCH_2CH_3$, Ph, $CH_2Ph$, $CONH_2$, $CSNH_2$ or $R_7$, $R_8$ and $R_9$ are respectively selected from any of H, F, Cl, Br, $NO_2$, OH, $CH_3$, $OCH_3$ and and $R_{10}$, $R_{11}$ and $R_{12}$ in the

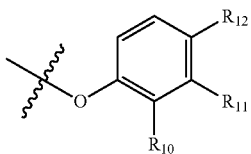

are respectively selected from any of H, F, Cl, Br, $NO_2$, OH, $CH_3$, $C_2H_5$, $OCH_3$, $OC_2H_5$, isopropyl, isobutyl, tert-butyl and tert-amyl.

In the above use, the feline coronavirus diseases are feline infectious peritonitis (FIP) caused by feline infectious peritonitis virus (FIPV).

Beneficial effects of the present invention:

Through researches, the present invention revealed for the first time that the bromophenol-pyrazoline compounds can inhibit the replication of the feline infectious peritonitis virus (FIPV). Clinical trials showed that the bromophenol-pyrazoline compounds can treat the feline infectious peritonitis (FIP) caused by the FIPV, etc., greatly improve the survival rate of cats, and can be used for preparing the drugs for treating the FIP.

DETAILED DESCRIPTION

Figure 1:
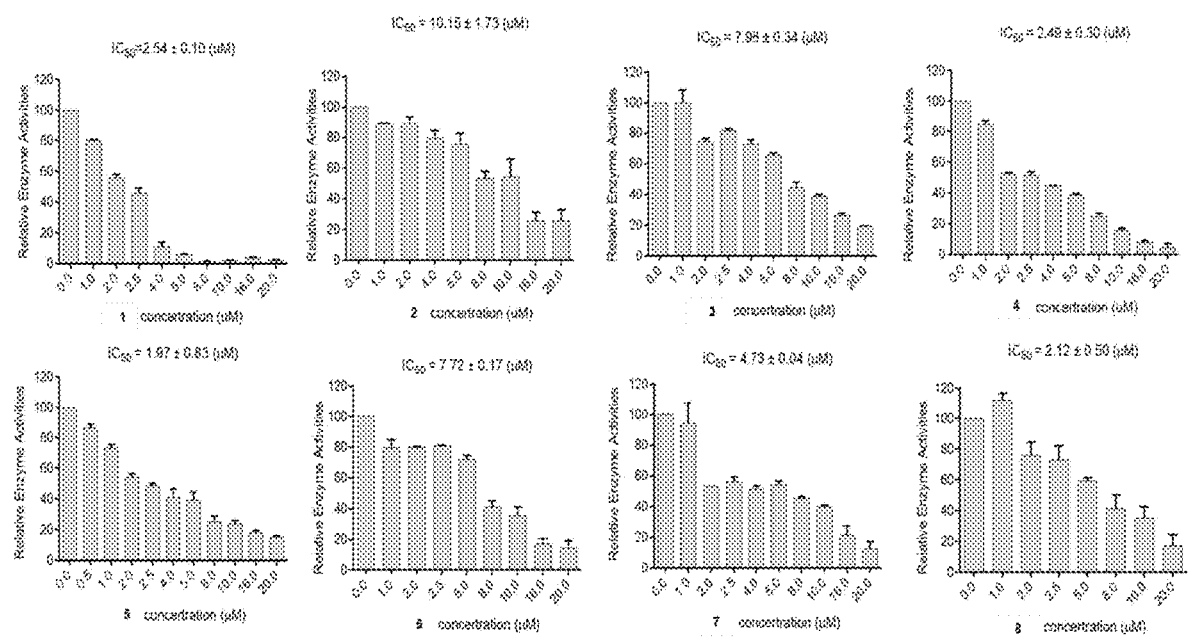
FIG. 1 shows determination results of inhibitory activity of compounds 1 to 8 provided in embodiments of the present invention against FIPV $M^{pro}$. The effects of different concentrations of the compounds on FIPV $M^{pro}$ activity were determined, and half-maximal inhibitory concentration ($IC_{50}$) values were determined by non-linear regression.

In order to facilitate understanding of the present invention, the present invention will be described in more detail below with reference to the accompanying drawings and specific embodiments. Preferred embodiments of the present invention are given in the detailed description. The present invention may, however, be embodied in many different forms, and should not be construed as limited to the embodiments set forth herein. Rather, these embodiments are provided to enable the disclosure to be understood thoroughly and completely.

It should be noted that the following detailed description is exemplary and is intended to provide further explanation of the present invention. Unless otherwise noted, all technical and scientific terms used herein have the same meaning as commonly understood by one of ordinary skill in the art to which the application belongs.

As described in the BACKGROUND, feline infectious peritonitis caused by feline infectious peritonitis virus (FIPV) has a very high fatality rate, but currently there is no effective drug for the feline infectious peritonitis.

In response to the outbreak of coronavirus pneumonia at the end of 2019, the inventors developed a bromophenol-pyrazoline compound capable of efficiently inhibiting a novel coronavirus (COVID-19) and having an effect of treating the coronavirus pneumonia (see Chinese Patent Publication No. CN111848516A for details). Subsequent studies revealed that bromophenol-pyrazoline compounds can treat porcine epidemic diarrhea and porcine transmissible gastroenteritis virus caused by porcine epidemic diarrhea virus (PEDV) and transmissible gastroenteritis coronavirus (TGEV) (see Chinese Patent Publication No. CN112472698A for details).

Although the FIPV and COVID-19, PEDV and TGEV belong to coronavirus, they are greatly different in terms of host, virus characteristics, types of infected cells, pathological tissues, pathogenic symptoms, etc.

(1) Hosts are different. The FIPV has low homology and distant relationship with COVID-19, PEDV and TGEV, and they have very different virus structures and have no cross-species infectivity. At present, no cross-species infection of human-derived coronaviruses, porcine coronaviruses and feline coronaviruses has been found.

(2) Virus characteristics are different. The FIPV are all derived from feline enteric coronavirus (FECV), and the FIPV in sick cats are not infectious. In contrast, COVID-19, PEDV and TGEV are highly infectious.

(3) Types of infected cells vary. The FIPV infects feline mononuclear macrophages, causing systemic immune system hyperresponsiveness. COVID-19 infects human lung cells, and the PEDV and TGEV infect porcine intestinal epithelial cells.

(4) Pathological tissues are different. FIPV can cause lesions in many tissues and organs of cats, such as serosa, kidney, mesenteric lymph nodes, brain, eye, liver, spleen and lung. COVID-19 causes pneumonia in human, and the PEDV and TGEV cause enteritis.

(5) Symptoms vary. The FIPV has a plurality of symptoms, comprising ascites, dyspnea, uveitis, ataxia, refractory fever, lethargy, anorexia, jaundice and weight loss. The symptoms of COVID-19 comprise fever, cough, chest distress and dyspnea. The symptoms of the PEDV and TGEV are diarrhea.

Therefore, the feline coronavirus FIPV, human coronavirus COVID-19, porcine coronavirus PEDV and TGEV belong to different types of viruses, and it is hard to predict functions and effects of substances capable of inhibiting human novel coronavirus and porcine coronavirus on feline coronavirus.

In order to further expand pharmaceutical field of the bromophenol-pyrazoline compounds, the inventors made a large number of attempts for the present invention, and unexpectedly found that the bromophenol-pyrazoline compounds have good inhibitory activity against the feline coronavirus and can inhibit replication of the FIPV; and clinical trials showed that the bromophenol-pyrazoline compounds can treat infectious peritonitis in cats caused by the FIPV, and greatly improve survival rate of cats, thus proposing the present invention.

In order to enable those skilled in the art to understand technical solution of the present application more clearly, the technical solution of the present application will be described in detail with reference to specific embodiments.

Test materials not specified in the embodiments of the present invention are all conventional test materials in the art and can be obtained from commercial sources.

Structural formulas of exemplary compounds 1-8 are shown below:

[Structures of compounds 1-8 shown as chemical diagrams]

Synthesis methods of the compounds 1-8 are described in the inventors' patent application CN111848516A.

Embodiment 1: Determination of inhibitory activity of bromophenol-pyrazoline compounds against feline infectious peritonitis virus main protease (FIPV $M^{pro}$)

(1) Expression and purification of FIPV $M^{pro}$

An FIPV $M^{pro}$ gene was inserted into a p GEX-6P-1 vector by conventional technical means such as PCR, enzymatic cleavage and ligation. The constructed vector was transformed into Escherichia coli BL21 (DE3) competent cells and cultured in LB containing 100 mg/mL ampicillin at 37° C. until OD600 of the cells reached 0.6. A total of 0.5 mM IPTG was used to induce protein expression at 16° C. for 16-18 hours. Collected cells were resuspended in suspension buffers (140 mM NaCl, 10 mM $Na_2HPO_4$, 2.7 mM KCl, 1.8 mM $KH_2PO_4$, 1 mM DTT, 10% glycerol, pH 7.3) and disrupted at high pressure and 4° C. Resulting cell debris was removed by centrifugation, a fusion protein of GST and FIPV $M^{pro}$ was enriched by a GST affinity medium, and GST tag at N terminal of the FIPV $M^{pro}$ was excised by PPase. Untagged FIPV $M^{pro}$ was further purified by Hi Trap Q (GE) and Superdex75 10/300 (GE), obtaining FIPV $M^{pro}$ with purity higher than 95%.

(2) Determination of FIPV $M^{pro}$ activity

The activity of FIPV $M^{pro}$ was determined by a buffer 50 mM Tris-HCl (pH 7.3), the FIPV $M^{pro}$ had a concentration of 1 μM, and a fluorogenic substrate was MCA-AVLQSGFR-Lys(Dnp)-Lys NH2 (coronavirus main protease fluorogenic substrate) having a concentrate of 40 μM, an excitation wavelength of 320 nm and a detection wavelength of 405 nm. Concentration gradients of the compounds 1-8 were 20 μM, 10 μM, 5 μM, 2.5 μM, 1 μM and 0.5 μM. Inhibitory effect of the compounds 1-8 on the FIPV main protease was determined separately.

(3) Determination results of inhibitory activity of the compounds against FIPV $M^{pro}$ As shown in FIG. 1, the bromophenol-pyrazoline compounds (1-8) showed significant inhibitory effect on the FIPV $M^{pro}$, and had a good application prospect in treating infectious peritonitis in cats.

Embodiment 2: Interference of replication of the FIPV virus in cells with the bromophenol-pyrazoline compounds To further confirm in vitro enzymatic inhibition results, the inventors evaluated whether the bromophenol-pyrazoline compounds could prevent FIPV replication in clinical wild-type FIPV-infected Crandell-Rees feline kidney (CRFK) cells.

Specific operations are as follows:

The CRFK cells were cultured with DMEM containing 8% fetal bovine serum in a cell incubator with 5% $CO_2$ at 37° C. When the cells grew to a density of about 80%, the cells were pretreated with 5 μM bromophenol-pyrazoline compounds to be tested for 1 hour, and then an FIPV wild strain (MOI=0.1) was inoculated into the CRFK cells. The CRFK cells inoculated with virus but without the compounds were set up as controls. After 24 hours, a cell supernatant was collected, and vRNA in the supernatant was subject to qRT-PCR analysis.

Figure 2:
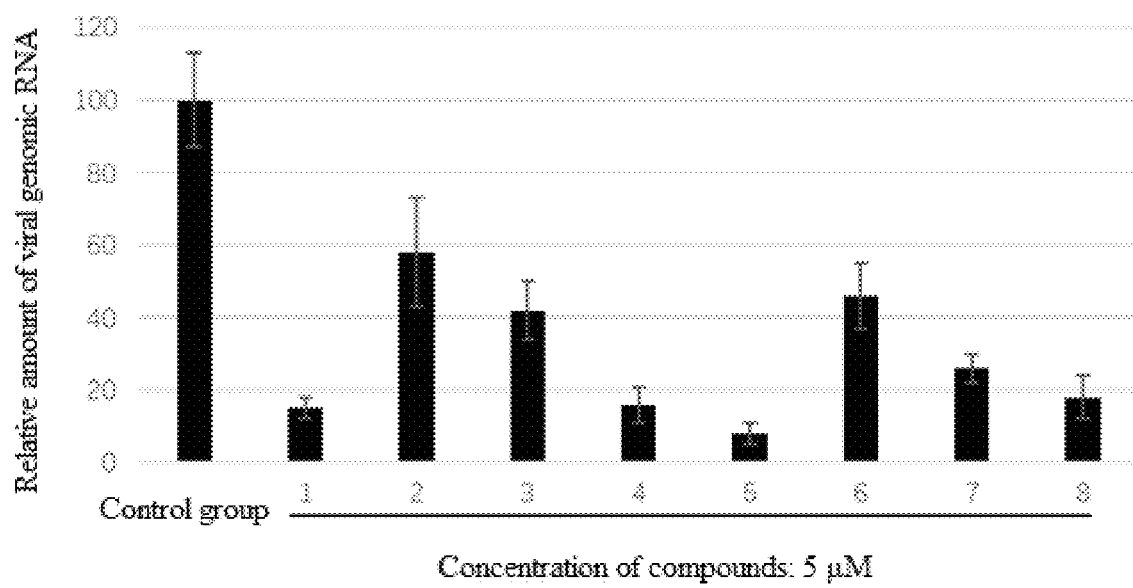
FIG. 2 shows the determination results of inhibiting FIPV replication in cells by the compounds 1-8 provided in the embodiments herein, for evaluating effects of different concentrations of the compounds on virus RNA replication.

Experimental results:

As shown in FIG. 2, the compounds 1-8 all showed strong ability to interfere with the FIPV virus replication in the CRFK cells infected with the wild-type FIPV at a concentration of 5 μM, with compound 5 having the strongest ability to inhibit FIPV virus replication.

Embodiment 3: Clinical trial of the compound 5 in the treatment of the feline infectious peritonitis (1) Detection of cats with the infectious peritonitis Serology or morphology cannot distinguish feline enteric coronavirus from the FIPV. According to the history, epidemiology, clinical symptoms, laboratory diagnosis, imaging examination and histopathological examination, the cats were diagnosed comprehensively after other diseases were ruled out. The FIPV infection was considered when the weight of sick cats gradually reduced, appetite decreased, body temperature increased, blood items showed mild non-regenerative anemia, lymphopenia, serum globulin concentration increased and albumin-globulin ratio significantly decreased compared with normal cats.

(2) Grouping in the clinical trial and treatment regimens

Thirty cats infected with the FIPV were divided into a wet FIP group (n=17) and a dry FIP group (n=13) according to presence of significant pleural effusion, ascites, dyspnea and other symptoms (fibrous pleurisy and peritonitis). The wet FIP group (17 cats) was randomly divided into a control group (3 cats), a GS-441524 group (6 cats) and a compound 5 group (8 cats). The dry FIP group (13 cats) was randomly divided into a control group (2 cats), a GS-441524 group (5 cats) and a compound 5 group (6 cats).

As shown in Table 1, all cats infected with the FIPV received symptomatic conventional treatment according to respective symptoms. For the wet and dry GS-441524 groups: 4.0 mg/kg was administered subcutaneously every 24 hours; and for the wet and dry compound 5 groups: 3 mg/kg was orally administered after dissolved in glucose solution once a day.

TABLE 1

Experimental grouping and treatment regimens of cats infected with the FIPV

| Experimental grouping | | | Number | Treatment regimen |
|---|---|---|---|---|
| Wet FIP group | | Control group | 3 | Conventional symptomatic treatment |
| | | GS-441524 group | 6 | Conventional symptomatic treatment + GS-441524 treatment |
| | | Compound 5 group | 8 | Conventional symptomatic treatment + compound 5 treatment |
| Dry FIP group | | Control group | 2 | Conventional symptomatic treatment |
| | | GS-441524 group | 5 | Conventional symptomatic treatment + GS-441524 treatment |
| | | Compound 5 group | 6 | Conventional symptomatic treatment + compound 5 treatment |

Rectal temperature was measured at least once a day, and body weight, respiration, appetite and activity were observed. Special people were arranged to feed the cats, and foodware was washed and disinfected every day. The cats with good appetite were fed with conventional cat food, and high protein pet food can was used as nutritional supplement. The cats with poor appetite were subject to nasal feeding and intravenous injection for nutritional supplement to ensure nutrition intake of the experimental cats. At the same time, defecation and urination were also observed in terms of volume and shape. The cats were examined for blood routine indexes, serum biochemical indicators and abdominal B ultrasound condition according to actual situation.

(3) Results of the clinical trial

Cases with good appetite, body weight, respiration, body temperature and other body conditions at the completion of 4-week treatment, and examined for the blood routine indexes and serum biochemical indicators twice (more than 1 week apart) were defined as effective.

The results of the clinical trial are shown in Table 2. In the Compound 5 treatment group, after 1 day of treatment, normal cat food was given, and the body temperature gradually decreased. After 7 days of treatment, the body temperature returned to normal, and the body weight increased. Ascites, dyspnea, jaundice and lymph nodes and other symptoms disappeared. Ocular lesions in some cats began to resolve significantly within 48 hours, and aqueous humor became clear. Compared with the positive drug GS-441524 group, the compound 5 treatment group had faster onset of action, fewer deaths and higher response rate. The above results show that the compound 5 can treat the infectious peritonitis in cats infected with the FIPV.

TABLE 2

Results of clinical trial in cats infected with the FIPV

| Experimental grouping | | Number | Death | Moderate response | Clinical manifestations |
|---|---|---|---|---|---|
| Wet FIP group | Control group | 3 | 3 | 0 | During the treatment, respiration and ascites were not significantly improved, the appetite gradually decreased, and all cats died after 20 days of treatment. |
| | GS-441524 group | 6 | 1 | 3 | After 3 days of treatment, the food intake recovered, and the body temperature gradually decreased. After 10 days of treatment, the food intake was normal, the body weight increased, and abdominal circumference decreased. |
| | Compound 5 group | 8 | 1 | 6 | After 1 day of treatment, the normal cat food was given, and after 3 days of treatment, the food intake returned to normal, and the body temperature decreased. The abdominal circumference gradually decreased, and such symptoms as ascites and dyspnea basically recovered after 10 days of treatment. |
| | Control group | 2 | 2 | 0 | During the treatment, fever and spasm were not significantly improved, symptoms of liver and kidney failure appeared, and the cats died soon after fasting. |
| Dry FIP group | GS-441524 group | 5 | 0 | 3 | After 3 days of treatment, the food intake recovered, and the body temperature gradually decreased. After 7 days of treatment, ordinary cat food was given, the body weight increased, and symptoms namely vomiting and diarrhea decreased. |
| | Compound 5 group | 6 | 0 | 5 | Normal cat food was given after 1 day of treatment, and the intake returned to normal after 3 days of treatment. After 7 days of treatment, the body temperature returned to normal, and the body weight increased. Such symptoms as jaundice and lymph node disappeared. The ocular lesions in some cats began to resolve significantly within 48 hours, and the aqueous humor became clear. |

The above description is directed to the preferred embodiments of the present invention, and is not construed as limitation thereto. Other modifications and changes may be devised by those skilled in the art without departing from the spirit and principle thereof. Any modification, equivalent replacement and improvement made within the spirit and principle of the present application should be included within the scope thereof.

What is claimed is:

1. A method of treating a feline coronavirus disease in a subject, comprising:
   administering to the subject in need thereof an effective amount of a bromophenol-pyrazoline compound of following formula:

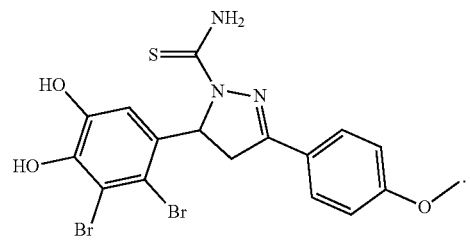 [SMILES: COc1ccc(C2=NN(C(N)=S)C(c3cc(O)c(O)c(Br)c3Br)C2)cc1]

2. The method of claim 1, wherein the feline coronavirus disease is feline infectious peritonitis (FIP) caused by feline infectious peritonitis virus (FTPV).

3. The method of claim 1, wherein the subject is a cat.

4. The method of claim 1, wherein an administration route is oral or subcutaneous.

5. A method of treating a feline coronavirus disease in a subject, comprising:
   administering to the subject in need thereof an effective amount of a bromophenol-pyrazoline compound of Formula (I):

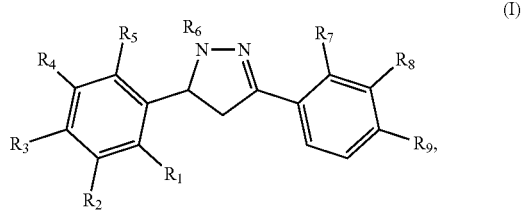

wherein $R_1$, $R_2$, $R_3$, $R_4$ and $R_5$ are independently selected from the group consisting of H, F, Br, OH and $OCH_3$;

$R_6$ is selected from the group consisting of H, CHO, $COCH_3$, $COCH_2CH_3$, $COCH_2CH_2CH_3$, $COOCH_3$, $COOCH_2CH_3$, phenyl (Ph), $CH_2Ph$, $CONH_2$, $CSNH_2$,

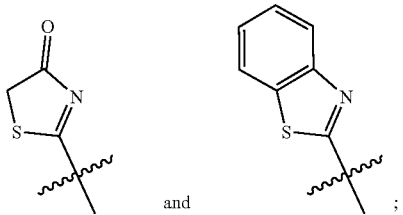 [SMILES: *C1=NC(=O)CS1 ; *c1nc2ccccc2s1]

and ;

and $R_7$, $R_8$ and $R_9$ are independently selected from the group consisting of H, F, Cl, Br, $NO_2$, OH, $CH_3$, $OCH_3$ and

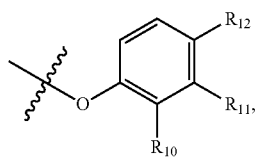

wherein $R_{10}$, $R_{11}$ and $R_{12}$ are independently selected from the group consisting of H, F, Cl, Br, $NO_2$, OH, $CH_3$, $C_2H_5$, $OCH_3$, $OC_2H_5$, isopropyl, isobutyl, tert-butyl and tert-amyl.

6. The method of claim 5, wherein the bromophenol-pyrazoline compound is selected from the group consisting of:

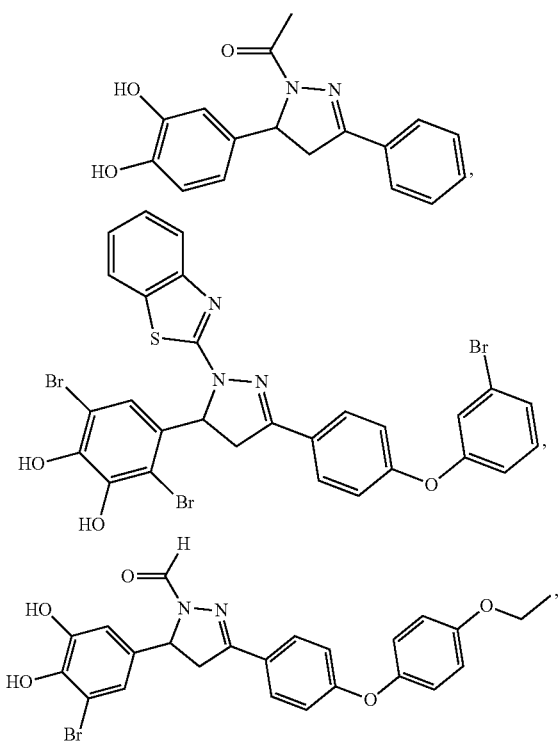

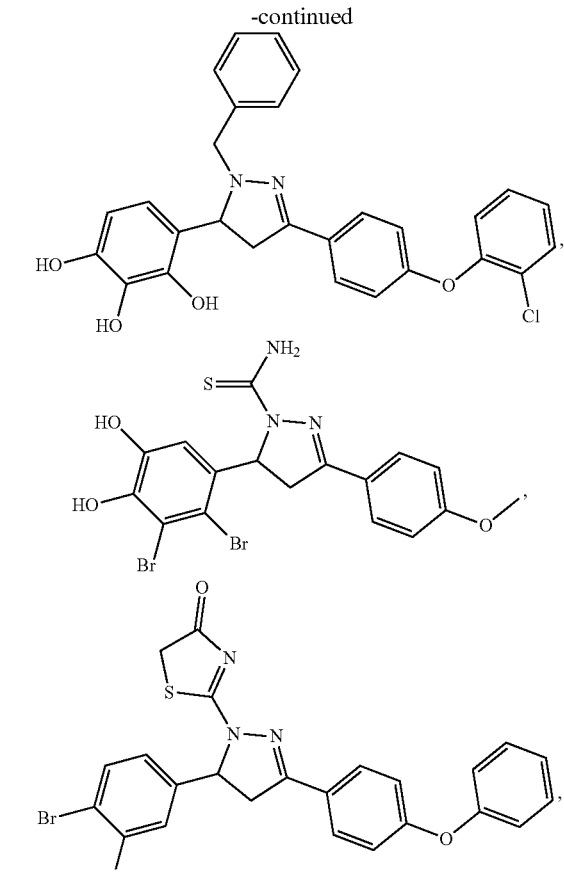

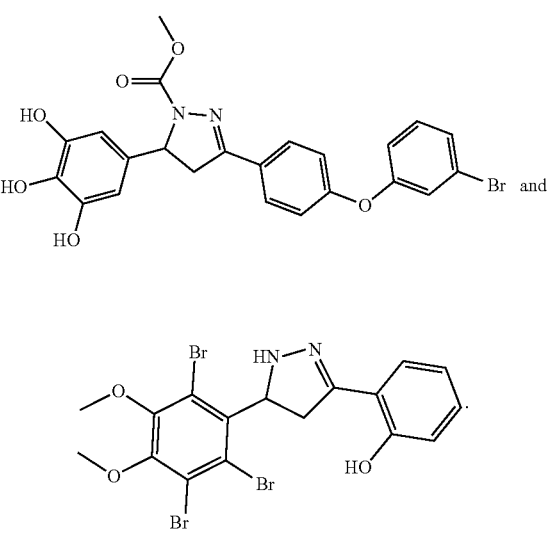 [SMILES: COC(=O)N1N=C(c2ccc(Oc3cccc(Br)c3)cc2)CC1c1cc(O)c(O)c(O)c1 ; COc1c(Br)c(Br)c(C2CC(c3ccccc3O)=NN2)c(Br)c1OC]

7. The method of claim 5, wherein the feline coronavirus disease is feline infectious peritonitis (FIP) caused by feline infectious peritonitis virus (FTPV).

8. The method of claim 5, wherein the subject is a cat.

9. The method of claim 5, wherein an administration route is oral or subcutaneous.

* * * * *